(12) United States Patent
Lei et al.

(10) Patent No.: US 10,369,094 B2
(45) Date of Patent: Aug. 6, 2019

(54) HYDROGEL CAPSULES AND PROCESS FOR PREPARING THE SAME

(71) Applicant: International Flavors & Fragrances Inc., New York, NY (US)

(72) Inventors: Yabin Lei, Holmdel, NJ (US); Li Xu, Edison, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 15/722,022

(22) Filed: Oct. 2, 2017

(65) Prior Publication Data

US 2018/0021241 A1 Jan. 25, 2018

Related U.S. Application Data

(63) Continuation-in-part of application No. 14/414,376, filed on Jan. 12, 2015, now Pat. No. 9,777,244.

(51) Int. Cl.

| | |
|---|---|
| A61K 8/06 | (2006.01) |
| A61K 8/81 | (2006.01) |
| A61K 9/50 | (2006.01) |
| A61Q 5/02 | (2006.01) |
| A61Q 5/06 | (2006.01) |
| A61Q 5/12 | (2006.01) |
| A61Q 15/00 | (2006.01) |
| A61Q 17/00 | (2006.01) |
| A61Q 19/10 | (2006.01) |
| A61K 8/11 | (2006.01) |
| C11D 3/50 | (2006.01) |

(52) U.S. Cl.
CPC ............ *A61K 8/8152* (2013.01); *A61K 8/068* (2013.01); *A61K 8/11* (2013.01); *A61K 8/8147* (2013.01); *A61K 9/5026* (2013.01); *A61Q 5/02* (2013.01); *A61Q 5/06* (2013.01); *A61Q 5/12* (2013.01); *A61Q 15/00* (2013.01); *A61Q 17/005* (2013.01); *A61Q 19/10* (2013.01); *C11D 3/50* (2013.01); *A61K 2800/412* (2013.01); *A61K 2800/5424* (2013.01); *A61K 2800/5426* (2013.01); *A61K 2800/56* (2013.01); *A61K 2800/624* (2013.01)

(58) Field of Classification Search
None
See application file for complete search history.

(56) References Cited

U.S. PATENT DOCUMENTS 5,476,660 A * 12/1995 Somasundaran ...... A61K 8/347
424/401
9,777,244 B2 * 10/2017 Lei ......................... A61Q 13/00
2003/0125222 A1 * 7/2003 Jahns ................... C11D 3/3703
510/130

FOREIGN PATENT DOCUMENTS

WO WO-2012075293 A2 * 6/2012 ............... A61K 8/11

* cited by examiner

*Primary Examiner* — Abigail Vanhorn
(74) *Attorney, Agent, or Firm* — Martin Zhang; XuFan Tseng; Elizabeth M. Stover

(57) ABSTRACT

This invention is a hydrogel capsule with a fragrance encapsulated therein during the polymerization process. The hydrogel capsule is of use in fabric care or personal care formulations.

19 Claims, No Drawings

HYDROGEL CAPSULES AND PROCESS FOR PREPARING THE SAME

BACKGROUND

Valuable chemical compounds such as fragrances have been encapsulated for protection, storage, and controlled release. Encapsulation refers to processes whereby an active ingredient is placed into a stabilized form. The release of active ingredient from the protected form may be rapid (such as by crushing, or by ingestion), or gradual (such as by dissolution, diffusion, or bio-degradation). In this manner it is possible to maximize the effectiveness of the active ingredient by ensuring that it is released at the proper time.

The term "microcapsule" has been used to describe small particles or beads having a size ranging from less than one micron to several millimeters, which may contain a wide variety of active ingredients (Thies (1994) *Today's Chemist* November p. 40; Goodwin (1974) *Chemtech Magazine* October p 623-26). Microcapsules refer to two broad groups: (1) "Aggregate" microcapsules having the active ingredient dispersed throughout a continuous matrix. The matrix may be a solid polymer or a gel swollen with solvent. In the case where the gel is swollen with water, the term "hydrogel" is applied. Hydrogel encapsulation systems of this type have been described and are generally based on cross-linked forms of water-soluble polymers such as alginate, gelatin, pectin, agar, gellan, or starch (Sanderson, et al. (1989) *Cereal Foods World* 34(12):993-998). (2) "Mononuclear" microcapsules, on the other hand, are composed of materials that show a true "shell-core" morphology. These are similar to an egg in that they have a solid shell or flexible membrane surrounding a core which may be a liquid, a solid, or even a gel.

U.S. Pat. No. 3,808,686 discloses the preparation of an organic solution of a water-insoluble, organic solvent soluble hydrophilic polymer for application to denture prostheses to eliminate denture breath. However, this preparation is strictly a matrix-based system, wherein the active ingredient is entrapped by physical absorption, which is not suitable for consumer applications such as personal care and fabric.

U.S. Pat. No. 3,660,563 discloses water-soluble polymers containing fragrances, drugs, soaps, etc. entrapped therein. However, this is a particle-based system that would not be able to retain fragrance oil in a base.

EP 1146057 discloses cross-linked polymeric nanoparticles for carrying skin care ingredients, e.g., fragrances, essential oils, etc. and food ingredients. However, this is, as claimed, a particle approach, wherein the fragrance is loaded in situ and the particle size is in the nanometer range, which would have poor stability in personal care and fabric application.

US 2002/0050659 teaches hydrocapsules for encapsulating a liquid, e.g., a solution, fluid, slurry, paste or suspension. However, the hydrocapsules of this document are coextruded and have low loading capacity and stability.

US 2012/0058929 teaches a microcapsule carrier system for fragrances, wherein the core of the microcapsule is composed of a fragrance and the shell is obtained by polymerizing one or more C1-C24 alkyl esters of acrylic acid and/or methacrylic acid; and methyl methacrylate (MMA), 1,4-butanediol diacrylate (BDA), pentaerthrityl triacrylate (PETIA) and/or ethylene glycol dimethacrylate (EDGMA). However, the microcapsules of this reference are small, have poor stability, and have a high level of polymer wall material compared to core material.

SUMMARY OF THE INVENTION

One aspect of this invention relates to a hydrogel capsule useful in a consumer product (e.g., a laundry care, personal care, therapeutic, cosmetic or cosmeceutic product).

The hydrogel capsule comprises a fragrance encapsulated in at least one polymerized acrylic or methacrylic acid, or ester thereof, in which the hydrogel capsule has a mean diameter in the range of 1 to 100 μm (e.g., 1 to 20 μm); the fragrance is encapsulated in the hydrogel capsule during polymerization of at least one acrylic or methacrylic acid, or ester thereof contained in an oil phase; the oil phase contains: (i) the fragrance (e.g., present at a level of 50 to 90% by weight of the oil phase), (ii) the at least one acrylic or methacrylic acid, or ester thereof (e.g., present at a level of 10 to 25% by weight of the oil phase), and (iii) a water-insoluble oil solvent selected from the group consisting of an isoparaffinic fluid, a caprylic triglyceride, a capric triglyceride, a light mineral oil, a light mineral wax, a vegetable oil, a light vegetable wax, diethylphthalate, butylbenzoate, benzylbenzoate, an ester solvent, triacetin, a glycol-based water-insoluble solvent, and a combination thereof; the at least one acrylic or methacrylic acid, or ester thereof is a multifunctional acrylate or methacrylate; and the multifunctional acrylate or methacrylate is further copolymerized with a monofunctional acrylate or methacrylate to form the shell of the hydrogel capsule. Typically, the ratio between the monofunctional acrylate or methacrylate and the multifunctional acrylate or methacrylate is up to 8:92.

A multifunctional acrylate or methacrylate contains two or more acrylate or methacrylate groups. Examples of the multifunctional acrylate or methacrylate are ethylene glycol diacrylate, ethylene glycol dimethacrylate, poly(ethylene glycol) dimethacrylate, 1,6-hexandiol dimethacrylate, and combinations thereof.

The multifunctional acrylate or methacrylate is copolymerized with a monofunctional acrylate or methacrylate to form the shell of the hydrogel capsule. A monofunctional acrylate or methacrylate contains only a single acrylate or methacrylate group. An example of the monofunctional acrylate or methacrylate is methyl methacrylate. The ratio between the monofunctional acrylate or methacrylate and the multifunctional acrylate or methacrylate can be up to 8:92 (e.g., 0.1:99.9 to 8:92 and 0.5:99.5 to 4:96).

The hydrogel capsule can be coated with a deposition aid selected from the group consisting of: polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, an acrylamidopropyltrimonium chloride/acrylamide copolymer, a methacrylamidopropyltrimonium chloride/acrylamide copolymer, sodium alginate, chitosan, tannic acid, and combinations thereof.

The deposition aid is typically present at a level of 0.5% to 10% by weight of the hydrogel capsule. Preferably deposition aids are polyquaternium-6, polyvinylamine, sodium alginate, chitosan, tannic acid, polyquaternium-7, polyquaternium-11, polyquaternium-22, polyquaternium-47, polyquaternium-37, polyquaternium-39, and any combination thereof.

In some embodiments, the hydrogel capsule further encapsulates an active material selected from the group consisting of a pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, or combination thereof.

In other embodiments, the hydrogel capsule further comprises a dispersant such as a polyvinyl alcohol (fully hydrolyzed or partially hydrolyzed), polystyrene sulfonate, carboxymethyl cellulose, sodium polystyrene sulfonate, alkylnaphthalenesulfonate formaldehyde condensate, polyvinylpyrrolidone, copolymer of vinyl pyrrolidone and quaternized dimethylaminoethyl methacrylate, oleth-10-phosphate, cetyltrimethylammonium chloride, ammonium lauryl ether sulfate, cocoamidopropylamine oxide, nonylphenol ethoxylate, quillaja saponin, N-lauroyl-L-arginine ethyl ester, sorbitan esters, lecithins, lyso-lecithins, polyethoxylated sorbitan esters, polyglyceryl esters, fatty acid esters, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof.

Another aspect of this invention relates to a delivery system comprising any one of the hydrogel capsules described above, e.g., in a slurry or solid form.

An optional component of the delivery system is a rheology modifier selected from the group consisting of alkali-swellable anionic acrylic polymer emulsion, anionic hydrophobically modified alkali-soluble acrylic polymer emulsion, anionic acrylic copolymer emulsion, hydrophobically-modified ethoxylated urethane, xanthan gum, carrageenan, gellan, pectin, hydroxyethyl cellulose, sodium carboxymethyl cellulose, guar, sodium alginate, fully exfoliated smectite clays, and combinations thereof.

The delivery system can further comprising a second, third, fourth, fifth, or sixth capsule, each of which having a microcapsule core encapsulated by a microcapsule wall. Each of these microcapsule walls is independently formed of an encapsulating polymer such as a sol-gel polymer, polyacrylate, polyacrylamide, poly(acrylate-co-acrylamide), polyurea, polyurethane, starch, gelatin and gum Arabic, poly(melamine-formaldehyde), poly(urea-formaldehyde), and a combination thereof.

Also with the scope of this invention are consumer products containing one of the hydrogel capsules or delivery systems described above. Exemplary consumer products are a laundry care, personal care, therapeutic, cosmetic and cosmeceutic product. The laundry care product can be a rinse conditioner, liquid detergent, powder detergent or fabric refresher.

Personal care products include shampoos, hair conditioners, leave-on hair products, hair rinses, antiperspirant deodorants, hand sanitizers, bar soaps, and body washes. The antiperspirant deodorant product can be formatted as a stick, roll-on or aerosol spray.

The method of producing the hydrogel capsule involves the steps of (a) providing an aqueous phase comprising an emulsifier; (b) providing an oil phase comprising at least one acrylic or methacrylic acid, or ester thereof, and a fragrance; (c) emulsifying the aqueous phase of (a) with the oil phase of (b) to obtain an emulsion; (d) polymerizing the emulsion to obtain a hydrogel capsule with a fragrance encapsulated therein; (e) curing the hydrogel capsule at room temperature; and (f) curing the hydrogel capsule, e.g., at an elevated temperature of at least 40° C., or more preferably in the range of 55 to 95° C., or 55 to 65° C. Step (e) is optional. In some embodiments, the hydrogel capsule is cured at an elevated temperature directly after step (d).

DETAILED DESCRIPTION OF THE INVENTION

This invention relates to a hydrogel capsule carrier for fragrances, the production thereof and the use of the carrier in providing a fragrance to a fabric care product or personal care product, e.g., antiperspirants, deodorants, hair conditioners, shampoos, leave-on hair care products, body lotions, and hair refreshers, as well as washing or cleaning compositions for laundry and surface treatment. The hydrogel capsules of this invention each contain a fragrance encapsulated in at least one polymerized acrylic or methacrylic acid, or ester thereof, wherein the fragrance is encapsulated in the hydrogel capsule during polymerization of the acrylic or methacrylic acid, or ester thereof. These hydrogel capsules enable the valuable active ingredient to be provided already distributed relatively homogeneously in a use mixture, without having to expose it to the other constituents during storage.

A fragrance is understood to mean all organic substances which have a desired olfactory property and are essentially nontoxic. This includes all fragrances used customarily in washing or cleaning compositions or in perfumery and includes fragrance mixtures or blends. A fragrance may be a compound of natural, semisynthetic or synthetic origin. Preferred fragrances can be assigned to the substance classes of the hydrocarbons, aldehydes or esters. The fragrances also include natural extracts and/or essences which may include complex mixtures of constituents, such as orange oil, lemon oil, rose extract, lavender, musk, patchouli, balsam essence, sandalwood oil, pine oil and cedar oil.

Nonlimiting examples of synthetic and semisynthetic fragrances include those described in WO 2016/049456 and US20150203787. Other active materials suitable for encapsulation are taste masking agents, taste sensates, malodor counteracting agents, vitamins, antibacterials, sunscreen actives, antioxidants, anti-inflammatory agents, anesthetics, analgesics, antifungal agents, antibiotics, anti-viral agents, anti-parasitic agents, anti-infectious and anti-acne agents, dermatological active ingredients, enzymes and co-enzymes, skin whitening agents, anti-histamines, chemotherapeutic agents, and insect repellents. In addition to the active materials listed above, the products of this invention can also contain dyes, colorants or pigments, naturally obtained extracts (for example paprika extract and black carrot extract), and aluminum lakes.

The higher C log P materials are preferred, meaning that those materials with a C log P value of 4.5 are preferred over those fragrance materials with a C log P of 4; and those materials with a C log P value of 4 are preferred over the fragrance materials with a C log P of 3.3.

The fragrance formulation of the present invention preferably have at least about 40 weight percent of materials with C log P greater than 3.3, preferably greater than about 80 and more preferably greater than about 90 weight percent of materials with C log P greater than 4.

In an additional embodiment, the fragrance formulation may contain fragrance materials with a C log P greater than about 1.5.

Those with skill in the art appreciate that fragrance formulations are frequently complex mixtures of many fragrance ingredients. A perfumer commonly has several thousand fragrance chemicals to work from. Those with skill in the art appreciate that the present invention may contain a single ingredient, but it is much more likely that the present invention will include at least eight or more fragrance chemicals, more likely to contain twelve or more and often twenty or more fragrance chemicals. The present invention also contemplates the use of complex fragrance formulations containing fifty or more fragrance chemicals, seventy five or more, or even a hundred or more fragrance chemicals in a fragrance formulation.

Preferably, the fragrance or the mixture of fragrances makes up at least 50% by mass, preferably 60 to 90% by mass, or more preferably 70 to 80% by mass of the oil phase used in preparing the hydrogel capsule of this invention.

In order to provide the highest fragrance impact from the fragrance encapsulated capsules deposited on the various substrates referenced herein, it is preferred that materials with a high odor-activity be used. Materials with high odor-activity can be detected by sensory receptors at low concentrations in air, thus providing high fragrance perception from low levels of deposited capsules. This property must be balanced with the volatility as described herein. Some of the principles mentioned above are disclosed in U.S. Pat. No. 5,112,688.

The polymerizable material used in the preparation of the hydrogel capsules of this invention is typically a monofunctional or multifunctional acrylic or methacrylic acid, or ester thereof. Such compounds are known and can be used in various proportions as blends or mixtures. Representative monofunctional monomers which can be employed according to this invention include but are not limited to acrylic acid, methacrylic acid, 2-hydroxyethyl acrylate, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-methylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate. Representative ester monomers of methacrylic acid, which can be used include 2-hydroxyethyl methacrylate, glycidyl methacrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, 2-(dimethylamino)ethyl methacrylate, 2-(diethylamino)ethyl methacrylate, 2-(diisopropylamino)ethyl methacrylate, N-(2-aminoethyl) methacrylamide hydrochloride, 2-aminoethyl methacrylate hydrochloride, N-(3-aminopropyl)methacrylamide hydrochloride, 2-(tert-butylamino)ethyl methacrylate and the like. The above monomers may be employed separately or in various mixtures according to this invention.

The use of multifunctional acrylate and methacrylate will lead to the formation of cross-linked network polymers upon polymerization. Such polymers have desirable properties such as good mechanical strength, elasticity, toughness, and flexibility. Examples of multifunctional acrylates and methacrylates of use in this invention include, but are not limited to, ethylene glycol dimethacrylate (EGDMA), trimethylolpropane trimethacrylate, trimethyloyl triacrylate, pentaerythritol triacrylate, pentaerythritol tetracrylate, bisphenol A dimethacrylate, di(trimethylolpropane) tetraacrylate (DTTA), 1-(acryloyloxy)-3-(methacryloyloxy)-2-propanol (AOMOP), trimethylolpropane ethoxylate triacrylate (TPETA), dipentaerythritol pentaacrylate, hexane diacrylate, poly(ethylene glycol) dimethacrylate (PEGDMA), and 1,6-hexandiol dimethacrylate (HDDMA), 1,4-butandiol dimethacrylate, 1,3-butandiol dimethacrylate, 1,6-hexandiol diacrylate, 1,4-butandiol diacrylate, 1,3-butandiol diacrylate. Preferably, this invention includes the use of multifunctional acrylates or methacrylate compounds such as EGDMA, PEGDMA, and HDDMA alone or in combination with one or more monofunctional acrylates or methacrylates.

The multifunctional acrylate or methacrylate is preferably copolymerized with a monofunctional acrylate or methacrylate (e.g., methyl methacrylate) to form the shell of the hydrogel capsule. Preferred multifunctional acrylate or methacrylate is ethylene glycol diacrylate, ethylene glycol dimethacrylate, poly(ethylene glycol) dimethacrylate, or 1,6-hexandiol dimethacrylate. The ratio between (i) the monofunctional acrylate or methacrylate (e.g., methyl methacrylate) and (ii) the multifunctional acrylate or methacrylate (e.g., ethylene glycol dimethacrylate) is desirably up to 8:92 with a lower limit of 0:100, 0.1:99.9, 0.5:99.5, and 1:99 and an upper limit of 8:92, 7:93, 6:94, and 5:95, such as 0:100 to 8:92, 0.1:99.9 to 8:92, 0.5:99.5 to 8:92, and 1:99 to 8:92.

Preferably, the acrylic or methacrylic acid, or ester thereof, makes up less than 25% by mass, preferably 5 to 20% by mass, or more preferably 10 to 15% by mass of the oil phase used in preparing the hydrogel capsule of this invention. In the hydrogel capsule, the polymeric material is typically present at a level of 0.5 to 10 wt %.

A capsule deposition aid from 0.01 to 25%, more preferably from 5 to 20% can be included by weight of the hydrogel capsule. The capsule deposition aid can be added during the preparation of the capsules or it can be added after the capsules have been made.

These deposition aids are used to assist the deposition of capsules to surfaces such as fabric, hair or skin. These include anionically, cationically, nonionically, or amphoteric water-soluble polymers. Suitable deposition aids include those described in WO 2016049456, pages 13-27. Additional deposition aids are described in US 2013/0330292, US 2013/0337023, and US 2014/0017278.

The hydrogel capsule is typically prepared in the presence of a capsule formation aid, which can be a surfactant or dispersant. Capsule formation aids also improve the performance of the microcapsule composition. Performance is measured by the intensity of the fragrance released during certain stages, e.g., the pre-rub and post-rub phases in laundry applications. The pre-rub phase is the phase when the capsules have been deposited on the cloth, e.g., after a wash cycle using a capsule-containing fabric softener. The post-rub phase is after the capsules have been deposited and are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and combinations thereof. The surfactant concentration in the capsule composition varies from 0.1 to 5% (e.g., 0.5 to 4%, 0.2 to 2%, and 1 to 2%).

Commercially available surfactants include, but are not limited to, sulfonated naphthalene-formaldehyde condensates such as MORWET D425 (naphthalene sulfonate, Akzo Nobel, Fort Worth, Tex.); partially hydrolyzed polyvinyl alcohols such as MOWIOLs, e.g., MOWIOL 3-83 (Air Products); ethylene oxide-propylene oxide block copolymers or poloxamers such as PLURONIC, SYNPERONIC or PLURACARE materials (BASF); sulfonated polystyrenes such as FLEXAN II (Akzo Nobel); ethylene-maleic anhydride polymers such as ZEMAC (Vertellus Specialties Inc.); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1).

Processing aids can also be used as capsule formation aids. They include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinyl-methylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with carboxymethyl cellulose ("CMC"), polyvinylpyrrolidone, polyvinyl alcohol, alkylnaphthalenesulfonate formaldehyde condensates, and/or a surfactant during processing to facilitate capsule formation. Examples of these surfactants include cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. In certain embodiments, the CMC polymer has a molecular weight range between about 90,000 Daltons to 1,500,000 Daltons, preferably between about 250,000 Daltons to 750,000 Daltons and more preferably between about 400,000 Daltons to 750,000 Daltons. The CMC polymer has a degree of substitution between about 0.1 to about 3, preferably between about 0.65 to about 1.4, and more preferably between about 0.8 to about 1.0. The CMC polymer is present in the capsule slurry at a level from about 0.1% to about 2% and preferably from about 0.3% to about 0.7%. In other embodiments, polyvinylpyrrolidone used in this invention is a water-soluble polymer and has a molecular weight of 1,000 to 10,000,000. Suitable polyvinylpyrrolidone are polyvinylpyrrolidone K12, K15, K17, K25, K30, K60, K90, or a mixture thereof. The amount of polyvinylpyrrolidone is 2-50%, 5-30%, or 10-25% by weight of the capsule delivery system. Commercially available alkylnaphthalenesulfonate formaldehyde condensates include MORWET D-425, which is a sodium salt of naphthalene sulfonate condensate by Akzo Nobel, Fort Worth, Tex.

The hydrogel capsule of this invention is produce by (a) providing an aqueous phase, which contains an emulsifier; (b) providing an oil phase, which contains at least one acrylic or methacrylic acid, or ester thereof, and a fragrance; (c) emulsifying the aqueous phase of (a) with the oil phase of (b) to produce an emulsion; (d) polymerizing the emulsion to produce a hydrogel capsule with a fragrance encapsulated therein; and (e) curing the hydrogel capsule.

The aqueous phase of the method includes an emulsifier and water. As is conventional in the art, an emulsifier is an agent used to bind together normally noncombinative substances, such as oil and water. It can be anionic, cationic or nonionic in nature. Examples of suitable emulsifiers include, but are not limited to, polyvinyl alcohol, e.g., a partially or completely hydrolyzed polyvinyl acetate (Biehn & Ernsberger (1948) *Ind. Eng. Chem.* 40:1449-1453), d-α-tocopheryl polyethylene glycol 1000 succinate (Mu & Feng (2003) *Pharma. Res.* 20:1864-1872), PLURACARE or poloxamer, or polyvinyl pyrrolidone. The PLURACARE block copolymers are synthetic copolymers of propylene oxide and ethylene oxide. In certain embodiments, the emulsifier is a hydrolyzed polyvinyl acetate such as a MOWIOL emulsifier manufactured by Hoechst A.G. (Frankfurt, Germany).

The oil phase of the method of this invention includes at least one acrylic or methacrylic acid, or ester thereof, as described above; multifunctional acrylate and methacrylate or ester, a fragrance as described above; and an oil. Exemplary oils of use herein include ISOPAR M (an isoparaffinic fluid) and the other ISOPAR variants available from ExxonMobile Corp.; caprylic and capric triglycerides (e.g., NEOBEE M-5, NEOBEE M-20, triglycerides of coconut oil; and NEOBEE 895, caprylic triglyceride, available from Stepan Chemicals), light mineral oils, light mineral waxes, vegetable oils, light vegetable waxes, diethylphthalate, butylbenzoate, benzylbenzoate, ester solvents, triacetin, and glycol-based water-insoluble solvents. The oil is present by weight of the oil phase at a level of 1 to 90% (e.g., 5 to 40% and 10 to 30%).

The weight ratio between the aqueous phase and oil phase can be 1:10 to 10:10 (e.g., 1:5 to 5:1 and 1:2 to 2:1).

Once the oil phase and aqueous phase are combined, the mixture is emulsified according to known techniques, e.g., homogenization, shaking, or exposure to ultrasound. Subsequently, the acrylic or methacrylic acid, or ester thereof, is polymerized to produce a hydrogel capsule with a fragrance encapsulated therein. Polymerization can be carried out using known methods of free radical polymerization. These include the use of initiators such as ammonium persulfate and azobis(isobutyronitrile) (AIBN), benzyl peroxide, and other catalysts such as sodium metabisulfate or tetramethylethylenediamine. Polymerization can be carried out at room temperature (e.g., 20-25° C.) for one to ten hours. The initiators and catalyst can be added in one-step, or intermittently, or in multiple steps.

The resulting hydrogel capsules are subsequently cured at an ambient temperature (e.g., 0 to 40° C.) for 0.5 to 48 hours (e.g., 1 hour, 3 hours, and 10 hours) or at an elevated temperature (e.g., at least 40° C., 55 to 95° C., and 55 to 65° C.) for 0.1 to 24 hours (e.g., 0.5 hours, 1 hour, 2 hours, and 4 hours). In some embodiment, the hydrogel capsules are cured at an ambient temperature and then at an elevated temperature.

Hydrogel capsules of this invention can also be additionally coated with a polymeric material, i.e., a deposition aid. The polymeric material can be anionic, cationic or nonionic. It can be added during the preparation of the capsules or after the capsules are made. Suitable polymeric polymers include MERQUAT 100 Polymer (polyquaternium-6; commercially available from Lubrizol, Cleveland, Ohio), SALCARE SC 96 (polyquaternium-37; BASF, Mount Olive, N.J.), MERQUAT 2200 (polyquaternium-7), LUPAMIN 9095 (polyvinylamine; BASF, Mount Olive, N.J.), ZEMAC E400 (a copolymer of ethylene and maleic anhydride with a number average molecular weight $M_n$ of about 95,000 and a weight average molecular weight of $M_w$ of 400,000; commercially available from Vertellus, Zeeland, Mich.), TICA-ALGIN HG 600 F (sodium alginate; TIC Gums, White Marsh, Md.), chitosan (Sigma-Aldrich, St. Louis, Mo.), tannic acid (Graham Chemical, Barrington, Ill.). Other exemplary polymeric polymers are polyquaternium-11 (Luviquat PQ 11 AT1; BASF), polyquaternium-22 (Merquat 280; Lubrizol), polyquaternium-47 (Merquat 2001; Lubrizol), polyquaternium-37 (Ultragel 300; BASF), polyquaternium-39 (Merquat 3940; Lubrizol), and any combinations thereof. Other suitable deposition aids include those described in WO 2016049456, pages 13-27. Additional deposition aids are described in US 2013/0330292, US 2013/0337023, and US 2014/0017278.

In some embodiments, the polymeric material is present at a level of 0.1% to 30% (e.g., 0.5 to 20% and 3 to 15%) to by weight of the hydrogel capsule.

Hydrogel capsules of this invention have a mean diameter in the range of 1 to 100 μm, more preferably in the range of 1 to 20 μm, most preferably in the range of 5 to 10 μm; and are stable during storage.

The hydrogel capsules of this invention are suitable for laundry care, personal care, therapeutic, cosmetic or cosmeceutic products. In particular, the hydrogel capsules of this invention are of particular use in wash-off products, which are understood to be those products that are applied for a given period of time and then are removed. Such products include laundry care products such as rinse conditioners, liquid detergent, powder detergent, and fabric refresher; as well as personal care products such as hair shampoos, hair conditioners, hair rinses, antiperspirant/deodorant, hand sanitizer, bar soaps, and body washes and the like. These products are well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, and 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

Personal care products, including cosmetic, cosmeceutic or pharmaceutical preparations can be formulated as "water-in-oil" (W/O) type emulsions, "oil-in-water" (O/W) type emulsions or as multiple emulsions, for example of the water-in-oil-in-water (W/O/W) type, as a PIT emulsion, a Pickering emulsion, a micro-emulsion or nano-emulsion. Emulsions that are particularly preferred are of the O/W type or W/O/W type.

In certain embodiments, the final composition or product may be in the form of an oil, a gel, a roll-on, a solid stick, a lotion, a cream, a milk, an aerosol, a spray, a powder, a foam, a shampoo, a hair conditioner, a lacquer or a make-up.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "include," "includes," and "including," are meant to be non-limiting.

The term "g" is meant to be gram or grams.

The terms "capsule" and "microcapsule" herein are used interchangeably.

The invention is described in greater detail by the following non-limiting examples. All publication cited herein are incorporate by reference in their entirety.

Example 1: Preparation of Hydrogel Capsules

A hydrogel capsule of this invention, i.e., Capsule 1, was prepared following the procedure below.

An emulsifier, 10 wt % MOWIOL 3-83 ("M-3-83"; Kuraray America Inc., New York, N.Y.), was prepared in aqueous solution by dissolving M-3-83 powder in water.

A water phase was prepared by diluting 20 g of 10% M-3-83 solution to 80 g of water, which was deoxygenated by bubbling $N_2$ for 30 minutes. In a separate container, 10 g of ethylene glycol dimethacrylate (EGDMA, Sigma-Aldrich) was added to 64 g of fragrance Posh Special (IFF, Union Beach, N.J.) and 16 g of NEOBEE M-5 (caprylic/capric triglyceride; Stepan, NORTHFIELD, Ill.) and purged with $N_2$ to form an oil phase. The aqueous and the oil phases were then combined and homogenized at 9500 rpm for 3 minutes to obtain a fragrance emulsion.

The fragrance emulsion was consequently purged with $N_2$, followed by adding 0.3 g of ammonium persulfate (APS, Sigma-Aldrich) aqueous solution in 4.7 g of water as the initiator. After 15 minutes, 5 g of a catalyst solution containing 0.4 g of sodium metabisulfate (Sigma-Aldrich) was added to start polymerization. The fragrance capsules were allowed to cure at 65° C. for up to three hours.

Example 2: Hydrogel Capsule with EGDMA/MMA

Capsule 2 of this invention was prepared following the procedure described in Example 1 above except that 8 g of EGDMA and 2 g of methyl methacrylate (MMA; Sigma-Aldrich) were used.

Example 3: Hydrogel Capsule with PEGDMA

Capsule 3 of this invention was prepared following the procedure described in Example 1 above except that 10 g of poly(ethylene glycol) dimethacrylate (PEGDMA, $M_w$=595, Sigma-Aldrich) was used instead of EDDMA.

Example 4: Hydrogel Capsule with HDDMA

Capsule 4 of this invention was prepared following the procedure described in Example 1 above except that 10 g of 1,6 hexanediol dimethacrylate (HDDMA, Sigma-Aldrich) was used instead of EDDMA. The average size of this capsule was about 8.7 μm.

Examples 5 and 6: Hydrogel Capsules with Different Dispersants

Capsules 5 and 6 were prepared following the procedure described in Example 1 except that PLURACARE® F127 and Pluronic® F68 Prill (both commercially available from BASF) were used, respectively.

Pluracare® F 127 NF Prill, a nonionic surfactant, is a copolymer of ethylene oxide and propylene oxide. This product has an average molecular weight of 12,600, a viscosity of 3,100 cP, and a pour/melt point of 56° C.

Pluronic® F68 Prill is polyoxypropylene-polyoxyethylene block copolymer.

Examples 7-14: Coated Hydrogel Capsules

To Capsule 1 obtained in Example 1 was added 120 g of 1% wt carboxymethyl cellulose (CMC, MW=250 kDa) aqueous solution. The resultant mixture was heated to 55° C. and cured at that temperature to obtain Capsule 7.

Hydrogel capsules coated with other polymers, Capsules 8-14, can be prepared in a similar fashion. Exemplary polymers are MERQUAT 100 Polymer (Polyquaternium-6; Lubrizol, Cleveland, Ohio), SALCARE SC 96 (Polyquaternium-37), MERQUAT 2200 (Polyquaternium-7), LUPAMIN 9095 (polyvinylamine; BASF, Mount Olive, N.J.), ZEMAC E400 (Vertellus, Zeeland, Mich.), TICA-ALGIN HG 600 F (Sodium alginate; TIC Gums, White Marsh, Md.), Chitosan (Sigma-Aldrich), Tannic acid (Graham Chemical, Barrington, Ill.).

Physical Characterization of Hydrogel Capsules

The above hydrogel Capsules 1-7, were characterized by microscopic techniques. This also allowed an assessment of the mechanical strength of the dried hydrogel capsules. SEM analysis clearly demonstrated that the hydrogel capsule retained its physical integrity under stress.

Examples 15-18: Consumer Products

The capsule slurry prepared in Example 1-14 can be blended into a consumer product and evaluated for its consumer benefits. These consumer product bases are commercially available to known in publications. Examples are fabric refresher base, laundry rinse conditioner base, a hand sanitizer (e.g., containing 62% ethanol), hair conditioner (e.g., an oil-free conditioner base commercially available from Magick Botanicals, Santa Ana, Calif.). The fragrance load is typically between 0.05 to 8% (e.g., 0.1 to 3%, 0.2 to 2%, and 0.5%) neat oil equivalent ("NOE"). A skilled person in the art can adjust the level of NOE in different consumer base based on known or improved evaluation protocols.

Example 19: AP/DEO (Antiperspirant Deodorant) Application

The above hydrogel capsules can be dispersed in an AP-roll base at 0.5% neat fragrance equivalent. The base typically contains 1 to 3% anionic surfactant, 10 to 20%, aluminium chlorohydrate, less than 1% silica, 1 to 2% *Helianthus annuus* and water. The hydrogel capsules may deliver excellent consumer benefits both in the pre- and post-rubbing stage.

Example 20: Deodorant and Antiperspirant

An exemplary wax-based deodorant is prepared by mixing paraffin wax (10-20%), hydrocarbon was (5-10%), white petrolatum (10-15%), acetylated lanolin alcohol (2-4%), diisopropyl adipate (4-8%), Mineral Oil (40-60%) and preservative (as needed); heating the mixture to 75° C. until melted, and, with stirring at 75° C., adding 4.0 parts by weight of an encapsulated fragrance of this invention.

An exemplary glycol/soap type deodorant is prepared by combining propylene glycol (60-70%), sodium stearate (5-10%), distilled water (20-30%) and 2,4,4-trichloro-2'-hydroxy diphenyl ether (0.01-0.5%); and heating the mixture, with stirring, to 75° C. until the sodium stearate has dissolved. The resulting mixture is cooled to 40° C. and encapsulated fragrance is added to the formulation.

An exemplary antiperspirant deodorant (soft solid) is prepared by combining cyclopentasiloxane (60%), dimethicone (10%), zirconium aluminum trichlorohydrex glycine (25%), encapsulated fragrance (2.5%) and fumed silica (2.5%).

Example 21: Body Wash

An exemplary body wash is composed of PLANTAPON 611 L (SLES, Cap Betaine, Lauryl Glycoside; 22%), ammonium lauryl sulfate (2.5%), LAMESOFT OP65 (Coco Glucoside, Glyceryl Oleate; 3%), polyquaternium 10-10 (0.5%), acrylates copolymer (0.5%), neat fragrance (0.3%), encapsulated fragrance (1%), DMDM hydantoin (0.3%), glycerin (3%) and water (q.s. 100%).

Example 22: Hair Products

An exemplary 2-in-1 hair shampoo is composed of sodium laureth sulfate (10%), cocamidopropyl betaine (7%), glyceryl stearate (2%), cetearyl alcohol (3%), panthenol (0.2%), acrylates copolymer (1.2%), dimethicone (1.5%), polyquaternium 10 (0.2%), encapsulated fragrance (1%), preservative (as needed), water (q.s. 100%), and NaOH to pH 6.0.

An exemplary hair gel is compose of PVP (3%), acrylates/C10-30 alkyl methacrylate copolymer (3%), denatured alcohol (10%), encapsulated fragrance (1%), Microcare PHG (0.5%), and water (q.s. 100%).

Example 23: Hand Sanitizer

An exemplary hand sanitizer is composed of acrylates C10-30 alkyl acrylate copolymer (0.2-0.5%), ethanol (60%), isopropanol (10%), glycerin (4%), encapsulated fragrance (1-5%), and water (q.s. 100%).

Example 24: Hydrogel Capsules HC-1

A hydrogel capsule of this invention, i.e., HC-1, was prepared following the procedure below.

Aqueous Phase Preparation.

An emulsifier solution, a 10 wt % aqueous solution of MOWIOL 3-83 (M-3-83, commercially available from Kuraray America Inc.), was prepared by dissolving solid M-3-83 in water under stirring at 60° C. for 3 hours. The 10% M-3-83 solution was used as a stock solution.

Preparation of Fragrance Emulsion.

A water phase was prepared by diluting 20 grams of 10% M-3-83 stock solution in 80 grams of water, which was then deoxygenated by bubbling $N_2$ for 30 minutes. In a separate container, 10 grams of ethylene glycol dimethacrylate (EGDMA, Aldrich) was added to a fragrance oil mixture containing 64 grams of Posh Special (IFF, Union Beach, N.J.) and 16 grams of Neobee M-5 oil to obtain an oil phase, which was purged with $N_2$ for 30 minutes. The aqueous phase and the oil phase were then combined and homogenized at 9500 rpm for 3 minutes to form a fragrance emulsion.

Preparation of Hydrogel Capsules.

After purging the fragrance emulsion with $N_2$ for 10 minutes, 5 grams of a water solution containing 0.3 g ammonium persulfate (APS, Sigma-Aldrich) as the initiator was added. After 15 minutes, 5 grams of a catalyst solution containing 0.4 gram sodium metabisulfate (Sigma-Aldrich) was added to the emulsion to start polymerization. The emulsion was kept at room temperature (~20° C.) for three hours and was then cured at 65° C. for three hours.

Example 25: Hydrogel Capsule HC-2 with EGDMA/MMA (99/1)

Hydrogel Capsule HC-2 was prepared following the procedure described in Example 24 except that 0.1 grams of methyl methacrylate (MMA, Aldrich) were added to the fragrance oil mixture together with 10 grams of EGDMA.

Example 26: Hydrogel Capsule HC-3 with EGDMA/MMA (95/5)

Hydrogel Capsule HC-3 was prepared following the procedure described in Example 24 except that 0.5 grams of methyl methacrylate (MMA, Aldrich) were added to the fragrance oil mixture together with 10 grams of EGDMA.

Example 27: Hydrogel Capsule HC-4 with EGDMA/MMA (90/10)

Hydrogel Capsule HC-3 was prepared following the procedure described in Example 24 except that 1 g of methyl methacrylate (MMA, Aldrich) were added to the fragrance oil mixture together with 9 g of EGDMA.

Performance Evaluation in a Hair Conditioner

To establish the performance of hydrogel capsules in a hair conditioner, each of HC-1 to HC-4 was independently blended into a model hair conditioner solution. The fragrance load was 0.5% neat oil equivalent ("NOE"). For comparison, the perfumery benefit of the capsules was evaluated by conducting a hair wash experiment using a standard protocol. Hairs were washed and air-dried for 16 hours before being evaluated by a panel of 12 judges. The fragrance intensity is rated from a LMS scale ranging from 0 to 10. A numerical value of 2 would suggest a modest intensity while a value of 10 indicates a strong intensity. The results are shown in Table 1 below.

TABLE 1

| Hair conditioner with hydrogel capsules | Unbrushing intensity | Post-brushing intensity | $I_{post}/I_{pre}$ |
|---|---|---|---|
| HC-1 | 2.5 | 5.75 | 2.3 |
| HC-2 | 3 | 5.5 | 1.8 |
| HC-3 | 2.88 | 6.25 | 2.2 |
| HC-4 | 1.88 | 1.93 | 1 |

Unexpectedly, HC-1, HC-2, and HC-3 (the capsules prepared with MMA/EGDMA up to 5:95) had a greater fragrance intensity than HC-4 (the capsule prepared with MMA/EGDMA at 10:90).

Example 28 and 29: Hydrogel Capsules HC-5 and HC-6 with PQ-11

Hydrogel Capsule HC-5 was prepared by adding to HC-1 (30 grams) slurry prepared in Example 27 3 g of POLYQUATERNIUM-11 (PQ-11, Vinyl pyrrolidone/dimethylaminoethyl methacrylate copolymer, a cationic polymer commercially available as LUVIQUAT PQ11 AT 1 from BASF, Ludwigshafen, Germany).

HC-6 was prepared by mixing 30 grams of HC-1 slurry and 7.5 g of PQ-11.

Performance in European Liquid Detergent Base

To establish the performance of HC-5 and HC-6, each capsule slurry was blended into a model European (EU) liquid detergent solution. The fragrance load was 0.5% neat oil equivalent. The perfumery benefit of the capsules was evaluated by conducting a laundry experiment using a standard protocol with a European wash machine. Terry towels were washed and air-dried for 16 hours before being evaluated by a panel of 12 judges. The fragrance intensity is rated from a LMS scale ranging from 0 to 35. A numerical value of 5 would suggest the fabric only produces a very week intensity while a value of 35 indicates the subject generates a strong intensity. The results are given in Table 2 below.

TABLE 2

| Liquid detergent with capsule | Pre-rubbing intensity | Post-rubbing intensity | $I_{post}/I_{pre}$ |
|---|---|---|---|
| HC-1 | 2.55 | 5.19 | 2.03 |
| HC-5 | 3.21 | 8.39 | 2.61 |
| HC-6 | 4.51 | 8.94 | 1.98 |
| Neat | 3.01 | 2.87 | 0.95 |

Unexpectedly, PQ-11 showed significant improvement on the fragrance intensity of hydrogel capsules.

Example 30-36: Hydrogel Capsules HC-7 to HC-13

Four adjuvants were used to prepare hydrogel capsules. See the adjuvants and their level in Table 3 below.

TABLE 3

| Capsule | Adjuvant | Chemical name | Concentration in capsule slurry |
|---|---|---|---|
| HC-7 | Polyquaternium-47 (MERQUAT 2001) | Acrylic acid/methacrylamidopropyl trimethyl ammonium chloride/methyl acrylate terpolymer, cationic polymer | 2% |
| HC-8 | Polyquaternium-37 (SALCARE SC 96) | Poly(2-methacryloxy-ethyltrimethyl-ammonium chloride), cationic polymer | 2% |
| HC-9 | Polyquaternium-7 (MERQUAT 2200) | Poly(acrylamide-co-diallyldimethyl-ammonium chloride), cationic polymer | 2% |
| HC-10 | Polyquaternium-22 (Merquat 295) | diallyl dimethyl ammonium chloride/acrylic acid copolymer, cationic polymer | 2% |
| HC-11 | Polyquaternium-6 (MERQUAT 100) | Poly(diallyldimethyl ammonium chloride), cationic polymer | 2% |
| HC-12 | Polyvinylamine (Lupamin 9095) | polyvinylamine molecular weight 340,000 Daltons | 2% |
| HC-13 | Polyquaternium-6 Polyvinylamine | | 1.5% 1% |

Performance in EU Liquid Detergent Base

Hydrogel capsules HC-7, HC-8, HC-9, and HC-10 were evaluated in a model European liquid detergent solution as described above. The results are shown in Table 4.

TABLE 4

| Detergent with Capsule | Pre-rubbing intensity | Post-rubbing intensity | $I_{post}/I_{pre}$ |
|---|---|---|---|
| HC-7 | 2.82 | 5.3 | 1.88 |
| HC-8 | 3.44 | 6.46 | 1.88 |
| HC-9 | 4.26 | 8.14 | 1.91 |
| HC-10 | 2.48 | 5.47 | 2.21 |
| Neat | 2.79 | 3 | 1.89 |

All hydrogel capsules showed better performance as compared to HC-1.

Performance in EU Fabric Conditioner Base

To establish the performance of the hydrogel capsules with performance aids, the capsule slurries each were blended into a model European fabric conditioner solution. The fragrance load was 0.5% neat oil equivalent. For comparison, a similar solution was prepared using neat fragrance oil at 0.5%, respectively. The perfumery benefit of the capsules was evaluated by conducting a laundry experiment using a standard protocol with a European wash machine. Terry towels were washed with the fabric conditioner loaded with a capsule and air-dried for 16 hours before being evaluated by a panel of 16 judges. The fragrance intensity is rated from a LMS scale ranging from 0 to 35. A numerical value of 5 would suggest the fabric only produces a very week intensity while a value of 35 indicates the subject generates a strong smell. The results are shown in Table 5 below.

TABLE 5

| Fabric conditioner with capsule | Pre-rubbing intensity | Post-rubbing intensity | $I_{post}/I_{pre}$ |
|---|---|---|---|
| HC-5 | 2.38 | 4.49 | 1.89 |
| HC-7 | 2.53 | 4.56 | 1.8 |
| HC-8 | 3.92 | 7.48 | 1.91 |
| HC-9 | 2.71 | 4.45 | 1.64 |
| HC-10 | 2.37 | 5.74 | 2.42 |
| Neat | 2.72 | 2.88 | 1.89 |

Performance in Hair Conditioner Base

To establish the performance of the hydrogel capsules in hair conditioners, the capsule slurries each were blended into a model hair conditioner solution. The fragrance load was 0.5% neat oil equivalent. The perfumery benefit of the capsules was evaluated by conducting a hair wash experiment using a standard protocol. Hairs were washed with the fragranced hair conditioner and were air-dried for 16 hours before being evaluated by a panel of 12 judges. The fragrance intensity is rated from a scale ranging from 0 to 35. A numerical value of 5 would suggest the hair only produces weak intensity while a value of 35 indicates the subject generates a very strong smell. The results are in Table 6 below.

TABLE 6

| Hair conditioner with capsule | Unbrushing intensity | Post-brushing intensity | $I_{post}/I_{pre}$ |
|---|---|---|---|
| HC-1 | 3.28 | 7.86 | 2.39 |
| HC-7 | 3.16 | 8.39 | 2.66 |
| HC-11 | 3.02 | 8.46 | 2.8 |
| HC-12 | 4.09 | 11.98 | 2.93 |
| HC-13 | 3.9 | 12.8 | 3.28 |

What is claimed is:

1. A hydrogel capsule comprising a fragrance encapsulated in at least one polymerized acrylic or methacrylic acid, or ester thereof, wherein
    the hydrogel capsule has a mean diameter in the range of 1 to 100 μm;
    the fragrance is encapsulated in the hydrogel capsule during polymerization of at least one acrylic or methacrylic acid, or ester thereof contained in an oil phase;
    the oil phase contains: (i) the fragrance, (ii) the at least one acrylic or methacrylic acid, or ester thereof, and (iii) a water-insoluble oil solvent selected from the group consisting of an isoparaffinic fluid, a caprylic triglyceride, a capric triglyceride, a light mineral oil, a light mineral wax, a vegetable oil, a light vegetable wax, diethylphthalate, butylbenzoate, benzylbenzoate, an ester solvent, triacetin, a glycol-based water-insoluble solvent, and a combination thereof;
    the at least one acrylic or methacrylic acid, or ester thereof is a multifunctional acrylate or methacrylate;
    the multifunctional acrylate or methacrylate is further copolymerized with a monofunctional acrylate or methacrylate to form the shell of the hydrogel capsule; and
    the ratio between the monofunctional acrylate or methacrylate and the multifunctional acrylate or methacrylate is up to 8:92 wherein the hydrogel capsule has a fragrance intensity greater than a hydrogel capsule prepared from a ratio greater than 8:92.

2. The hydrogel capsule of claim 1, wherein the hydrogel capsule is coated with a deposition aid selected from the group consisting of: polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, an acrylamidopropyltrimonium chloride/acrylamide copolymer, a methacrylamidopropyltrimonium chloride/acrylamide copolymer, sodium alginate, chitosan, tannic acid, and combinations thereof.

3. The hydrogel capsule of claim 1, wherein the hydrogel capsule has a mean diameter in the range of 1 to 20 μm; and the oil phase contains: (i) 50 to 90% of the fragrance, and (ii) 10 to 25% of the at least one acrylic or methacrylic acid, or ester thereof.

4. The hydrogel capsule of claim 2, wherein the deposition aid is present at a level of 0.5% to 10% by weight of the hydrogel capsule.

5. The hydrogel capsule of claim 1, wherein the multifunctional acrylate or methacrylate is ethylene glycol diacrylate, ethylene glycol dimethacrylate, poly(ethylene glycol) dimethacrylate, 1,6-hexandiol dimethacrylate, or a combination thereof.

6. The hydrogel capsule of claim 5, wherein the multifunctional acrylate or methacrylate is ethylene glycol dimethacrylate.

7. The hydrogel capsule of claim 1, wherein the monofunctional acrylate or methacrylate is methyl methacrylate.

8. The hydrogel capsule of claim 1, wherein the hydrogel capsule further encapsulates an active material selected from the group consisting of a pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, or combination thereof.

9. A hydrogel capsule of claim 1, further comprising a dispersant selected from the group consisting of a polyvinyl alcohol, polystyrene sulfonate, carboxymethyl cellulose, sodium polystyrene sulfonate, alkylnaphthalenesulfonate formaldehyde condensate, polyvinylpyrrolidone, copolymer of vinyl pyrrolidone and quaternized dimethylaminoethyl methacrylate, oleth-10-phosphate, cetyltrimethylammonium chloride, ammonium lauryl ether sulfate, cocoamidopropylamine oxide, nonylphenol ethoxylate, quillaja saponin, N-lauroyl-L-arginine ethyl ester, sorbitan esters, lecithins, lyso-lecithins, polyethoxylated sorbitan esters, polyglyceryl esters, fatty acid esters, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof.

10. A delivery system comprising a hydrogel capsule of claim 1 in a slurry or solid form.

11. The delivery system of claim 10, further comprising a rheology modifier selected from the group consisting of alkali-swellable anionic acrylic polymer emulsion, anionic hydrophobically modified alkali-soluble acrylic polymer emulsion, anionic acrylic copolymer emulsion, hydrophobically-modified ethoxylated urethane, xanthan gum, carrageenan, gellan, pectin, hydroxyethyl cellulose, sodium carboxymethyl cellulose, guar, sodium alginate, fully exfoliated smectite clays, and combinations thereof.

12. The delivery system of claim 10, further comprising a second, third, fourth, fifth, or sixth capsule, wherein each of these capsules has a microcapsule core encapsulated by a microcapsule wall, and the microcapsule wall is independently formed of an encapsulating polymer selected from the group consisting of a sol-gel polymer, polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof.

13. A consumer product comprising the hydrogel capsule of claim 1.

14. The consumer product of claim 13, wherein said consumer product is a laundry care, personal care, therapeutic, cosmetic or cosmeceutic product.

15. The consumer product of claim 14, wherein the personal care product is a hair shampoo, hair conditioner, leave-on hair products, hair rinse, antiperspirant deodorant, hand sanitizer, bar soap or body wash.

16. The consumer product of claim 15, wherein antiperspirant deodorant product is formatted as a stick, roll-on or aerosol spray.

17. The consumer product of claim 14, wherein the laundry care product is a rinse conditioner, liquid detergent, powder detergent or fabric refresher.

18. A consumer product comprising the delivery system of claim 10.

19. The consumer product of claim 18, wherein said consumer product is a laundry care, personal care, therapeutic, cosmetic or cosmeceutic product.

* * * * *